United States Patent [19]

Walkowiak et al.

[11] 4,369,262
[45] Jan. 18, 1983

[54] DENTAL MATERIAL BASED ON CROSSLINKED PLASTIC AND POLYMERIZABLE BINDER

[75] Inventors: Michael Walkowiak, Leverkusen; Wolfgang Podszun, Cologne; Bernhard Leusner, Leverkusen; Carlhans Süling, Odenthal; Hans-Hermann Schulz, Leichlingen, all of Fed. Rep. of Germany

[73] Assignee: Bayer Aktiengesellschaft, Leverkusen, Fed. Rep. of Germany

[21] Appl. No.: 283,761

[22] Filed: Jul. 16, 1981

Related U.S. Application Data

[63] Continuation of Ser. No. 95,737, Nov. 19, 1979, abandoned.

[30] Foreign Application Priority Data

Nov. 24, 1978 [DE] Fed. Rep. of Germany ...... 2850916

[51] Int. Cl.$^3$ .............................................. A61K 6/08
[52] U.S. Cl. ........................................ 523/109; 524/533; 525/226; 525/228; 525/297; 525/308; 525/309
[58] Field of Search .............. 523/109; 525/226, 228, 525/297, 308, 309; 524/533

[56] References Cited

U.S. PATENT DOCUMENTS 3,628,988 12/1971 Stol et al. .......................... 525/226
4,134,930 1/1979 Kubota ................................ 106/35

Primary Examiner—Harold D. Anderson
Attorney, Agent, or Firm—Sprung, Horn, Kramer & Woods

[57] ABSTRACT

The invention includes dental materials based on organic plastics in paste form, comprising at least one phase consisting essentially of finely divided, crosslinked plastics which contain copolymerized ester(s) of methacrylic acid to the extent of at least 50% by weight, and the second phase consisting essentially of ester(s) of methacrylic acid to the extent of at least 50% by weight. The materials can be used for making prostheses, crowns, bridges, artificial teeth, dental fillings, etc.

5 Claims, No Drawings

DENTAL MATERIAL BASED ON CROSSLINKED PLASTIC AND POLYMERIZABLE BINDER

This is a continuation of application Ser. No. 095,737, filed Nov. 19, 1979, now abandoned.

The present invention relates to novel dental materials based on organic plastics.

The use of plastics as a material for prostheses, crowns, bridges artificial teeth and dental fillings is generally known. Organic materials for dental fillings are usually used as formulations of polymers and polymerisable binders. Because of their consistency and tackiness, these mixtures have technological and clinical disadvantages.

Because of their consistency, the organic materials which were hitherto customary are wiped into the cavity. In many cases some of the compositions introduced are stripped from the wall of the cavity after filling due to adhesion to the filling instrument. This phenomenon cannot as a rule be detected by the dentist and thus leads to nonparietal incomplete fillings, with the known disadvantages of them.

The increased tackiness of the filling materials known hitherto has a particularly adverse effect in the case of multi-surface cavities. Thus, as is known from the amalgam filling technique, perfect filling of the cavity is only possible if a filling material is introduced in portions. In this filling technique, small portions are first pressed parietally into the angles of the cavity, and only then is the cavity filled.

In order to compensate for the severe polymerization shrinkage of previous organic filling materials, it was necessary to allow the material to harden in the cavity in portions, which is a very time-consuming technique.

Another disadvantage of the organic filling materials known hitherto was the poor bonding to the cavity wall. It was also impossible to increase the adhesion substantially by using aid etching technique or applying retention pins.

Whilst in the case of single-surface fillings in the region of the front teeth the shape of the surface is achieved by applying moulding strips, the shaping of occlusal surfaces with materials which have a tacky consistency presents difficulties. Thus the areas of the masticating surfaces could be shaped only coarsely in the case of materials known hitherto. Shaping by rotating abrasive and polishing instruments was thus usually required after hardening. As is known, damage to the adjacent enamel areas is as a rule unavoidable during this process. The results of this are distortions in the relief of the masticating surface and in some cases occlusal disturbances.

Attempts have been made to produce the desired shape of the surface by producing a "carvable" consistency. However, this "carvable" property only results when a certain degree of polymerisation has already been achieved. If the filling material is worked in this state, the filling surface can crack open or tear and thus damage to the filling cannot be excluded. These cracks, produced by "carving", can be openings for microorganisms and for dyestuffs, with the known effects. Moreover, working of materials which are already partly polymerised can lead to interference with the polymerisation.

According to the present invention there is provided a dental material based on organic plastics in paste form, in which at least one phase consists essentially of finely divided, crosslinked plastics which contains copolymerised ester(s) and the second phase consists of polymerisable binders, which consist essentially of ester(s) of methacrylic acid to the extent of at least 50% by weight.

It has been found, surprisingly, that these pastes, and especially those in which the finely divided, crosslinked plastics are polymer beads with an average particle size of 10–100μ, are outstandingly suitable as a dental filling material. Preferably the dental material contains 50 to 75% by weight of finely divided crosslinked plastics.

The materials according to the invention can be prepared in a consistency which makes processing as is customary in the amalgam filling technique possible, that is to say they can be (a) pressed in and (b) shaped.

The following remarks relate to the aspect (a) of filling technique:

With the materials according to the invention, it is possible, using a non-tacky, firm consistency which is suitable for pressing in, to fill single-surface and multi-surface cavities parietally in several portions. The special property of the material means that there is no formation of layers when filling is effected in portions, that is to say the individual portions bond to one another homogeneously.

After introduction of a particular portion into the cavity and the pressing-in or adapting thereof, this portion remains in position without changing its shape, that is to say it cannot even be deformed elastically.

Furthermore, because of the special consistency, the cavity can be filled using so-called amalgam guns without the filling material being pulled off again from the wall of the cavity or continuing to adhere to the nozzle of the gun.

The following remarks relate to the aspect (b) of filling technique:

The materials according to the invention exhibit a consistency which allows shaping by instruments and is already obtained immediately after the mixing process. This consistency makes it possible for the occlusal individual form of the masticating surface to be shaped, after filling the cavity, by means of suitable instruments, for example of plastic or of metal, such as are used in the amalgam filling technique.

The paste-like dental materials, according to the invention, based on organic plastics, are transformed, by hardening, into solid substances which can readily be polished.

For the preparation of the dental materials in accordance with the invention, from 40 to 80, and preferably from 50 to 75, parts by weight of finely divided crosslinked plastic, from 25 to 50 parts per weight polymerizable binder, and from 0.01 to 5 wt. % initiators are mixed to form a paste.

To facilitate paste preparation, inhibitors, light stabilizers and/or up to 5 parts by weight amorphous silicic acid may be added. For specific indications, it may be advisable to add also dyes.

Suitable finely divided, crosslinked plastics for the paste-like formulations according to the invention are solid, comminuted, appropriately pulverulent crosslinked polymers which contain at least 50% by weight of copolymerised esters of methacrylic acid, preferably methacrylic acid methyl ester. The fine-particled, crosslinked polymer can be in form of polymer chips or in the form of an emulsion polymer, or particularly advantageously in the form of a bead polymer, in which case the average particle size of the bead polymer should preferably be between 10 and 100μ.

Suitable crosslinking agents are the polyvinyl compounds which can be copolymerised with methyl methacrylate, such as, for example, ethylene glycol dimethacrylate and divinylbenzene, and the proportion of crosslinking agent should be 2 to 35% by weight of the monomer mixture. Besides the crosslinking agent, other monomers can be copolymerised in the organic filler substance, for example in order to influence the swelling properties of the filler substance or in order to modify the mechanical properties of the hardened dental plastic.

Bead polymers having a mean bead diameter of from 10 to 200μ of one or more polymerized vascous methacrylates and/or dimethacrylates having a viscosity of from 0.5 to 500 Pa.s and, optionally, up to 20% by weight of one or more other vinylmonomers, are also particularly suitable for the paste formation.

Polymer beads having an average bead diameter of from 5 to 500μ, consisting of an inorganic fine-particled filler and polymerized (meth)acrylic acid esters, and a process for their production, wherein a mixture of monomer and polymer which is optionally soluble in the monomer, which has a viscosity of from 0.1 to 10 Pa.s, measured at the dispersion temperature, and filler is suspended in an aqueous medium in the presence of dispersants and is polymerized, are also particularly suitable for the paste formation.

Suitable esters of methacrylic acid are those of monohydric and polyhydric alcohols, optionally mixed with other vinyl monomers, on condition that the content of esters of methacrylic acid must be at least 50% by weight. Preferably the finely divided crosslinked plastics are built up from ester(s) of methacrylic acid to the extent of more than 80% by weight. Preferably the second phase comprises more than 80% by weight of ester(s) of methacrylic acid.

Examples of suitable esters of methacrylic acid which may be mentioned are aliphatic (e.g. alkyl of 1–4 carbon atoms) and cycloaliphatic esters (e.g. cycloalkyl of 4–7, preferably 5–6 ring members), such as methyl methacrylate, ethyl methacrylate and cyclohexyl methacrylate.

Very particularly suitable binders are furthermore esters of polyhydric alcohols (particularly alkylene, especially ethylene or propylene glycols having 1 to 4 or more alkylene units) with a molecular weight of 190–10 000, especially esters of bivalent and trivalent alcohols with a molecular weight of 190–800, such as, for example, ethylene glycol dimethacrylate, triethylene glycol dimethacrylate, neopentylglycol dimethacrylate or trimethylolpropane trimethacrylate, and moreover urethane and ureidopolymethacrylates, which are accessible by reacting a hydroxyalkyl methacrylate or an aminoalkyl methacrylate with polyisocyanates, for example the compound of the formula $$CH_2=\overset{CH_3}{\underset{|}{C}}-COO(-CH_2)_2-OOC-NH-(CH_2)_6-NH-COO-(CH_2)_2-OOC-\overset{CH_3}{\underset{|}{C}}=CH_2$$

Very good pastes are obtained if at least a proportion of the esters of methacrylic acid used consists of compounds of the bis-DMA type, of the formula

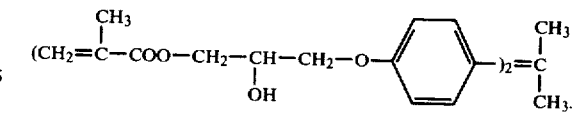

Dental filling compositions with a good consistency and a high level of mechanical strength are obtained, in particular, if mixtures of various methacrylic acid esters are used as the esters of methacrylic acid, especially mixtures of 20–70 parts by weight of Bis GMA and BO–80 parts by weight of triethylene glycol dimethacrylate.

The customary starter systems can be used for hardening the dental materials according to the invention, that is to say systems which supply free radicals, anions or cations and which can trigger off free radicals, anionic or cationic polymerization. Peroxides or aliphatic azo compounds are particularly suitable in the case of systems which supply free radicals, for example, benzoyl peroxide, lauroyl peroxide or azoisobutyric acid dinitrile, which mornally are used in amounts ranging from 0.1 to 5 wt.%. While the cure at elevated temperature is carried out with the acid of peroxides or other radical initiators alone, curing at room temperature requires the addition of accelerators, preferably aromatic amines. Suitable accelerators are N-N-substituted toluidines and xylidines, such as NN-dimethyl-p-toluidine or NN-bis(2-hydroxyethyl)xylidine. A good cure is obtained with an 0.5 to 3% amine addition. An advantageous form for a peroxide/accelerator-activated system is the two-paste form, one of the pastes incorporating the radical initiator and the other the accelerator, and curing being initiated by mixing of the two pastes.

Curing by means of UV light or visible light, with appropriate sensitization, is also a very good method. Suitable photoinitiators are, for example, benzophenone and its derivatives, benzoin and its derivatives such as benzoin ether, anthraquinone, and aromatic disulfides.

In addition to hardening with light in the visible range or UV range, hardener systems based on redox systems, for example based on peroxide/amine, are particularly suitable for dental filling compositions.

EXAMPLE 1

Preparation of a bead polymer from methyl methacrylate and ethylene glycol dimethacrylate

Polymerisation

Reaction vessel: 6 liter autoclave with a double-anchor stirrer

Solution I: 2,500 ml of distilled water (Dispersing agent solution): 500 ml of a 7.5% strength aqueous solution of the copolymer of 1 part by weight of methacrylic acid and 1 part by weight of methyl methacrylate, with a pH of 6 and a viscosity of 3,650 cp.

Solution II: 690 g of methyl methacrylate, 60 g of ethylene glycol dimethacrylate, 3.75 g of benzoyl peroxide and 3.75 g of lauroyl peroxide.

Solution I is initially introduced into the autoclave and is stirred for 5 minutes. Solution II is added all at once, with the stirrer stopped, and the autoclave is flushed with nitrogen. The pressure is then increased to 5 bars of nitrogen, the stirrer speed is adjusted to 400 rpm and the mixture is heated to 80° C. When the exothermic reaction starts, the mixture is cooled to an extent such that the temperature remains below 90° C. The mixture is subsequently stirred at 80° C. for 2 hours.

Working up

The mixture is let down and diluted to 10 l with distilled water. After adding 180 g of glacial acetic acid, it is heated to 90°-100° C. for 15 minutes. The bead polymer which precipitates is filtered off after cooling, washed by stirring three times in 5 l of distilled water at a time, and dried at 60° C.
Yield: 645 g
Average bead diameter: 25μ.

EXAMPLE 2

Preparation of a bead polymer of methyl methacrylate, divinylbenzene and ethylvinylbenzene Solution I (dispersing agent solution): 2250 ml of distilled water and 750 ml of the 7.5% strength copolymer solution according to Example 1
Solution II: 685 g of methyl methacrylate, 106.5 g of divinylbenzene (60% strength in ethylvinylbenzene), 3.75 g of benzoyl peroxide and 3.75 g of lauroyl peroxide.

The polymerisation and working up are carried out as in Example 1
Yield: 640 g,
Average particle size: about 40μ.

EXAMPLE 3

Paste-like dental materials according to the invention

(A) Peroxide paste 320 g of the bead polymer from Example 1, 112 g of bis-GMA ("Nupol" 46-4005 from Messrs. Freeman Chemical), 68 g of triethylene glycol dimethacrylate and 3.6 g of benzoyl peroxide.

The individual components are put into a kneader and kneaded intensively for 60 minutes, a vacuum of about 20 mm Hg being applied during the last 10 minutes. A kneadable mass with a particularly firm consistency is obtained in this manner.

(B) Amine paste

The bead polymer, bis-GMA and triethylene glycol dimethacrylate are employed in the same amounts as in the case of the peroxide paste (A), and are processed. However, instead of the peroxide, 3.6 g of N,N-bis-(2-hydroxypropyl)-3,5-dimethylaniline are employed.

(C) Paste-like composition for filling teeth

Equal parts (for example 200 mg each) of the amine paste and peroxide paste are mixed intensively for 30 seconds. The resulting mixture is outstandingly suitable as a dental filling material. It hardens in a few minutes with a little shrinkage on polymerisation.

EXAMPLE 4

Paste-like dental material according to the invention

An amine paste and a peroxide paste are prepared from 330 g of the bead polymer according to Example 2, 134 g of bis-GMA, 66 g of triethylene glycol dimethacrylate and 4 g of benzoyl peroxide or, respectively, 3 g of N,N-bis-(2-hydroxypropyl)-3,5-dimethylaniline, by a procedure corresponding to that in Example 3.

This material is mixed like the material from Example 3. A mixture which is outstandingly suitable as a dental filling mixture is likewise obtained.

EXAMPLE 5

Pasty dental material in accordance with the invention

A mixture is prepared by the procedure set forth in Example 3 from
300 g bead polymer according to Example 1,
112 g bis-GMA,
68 g triethylene glycol dimethacrylate, and
0.9 g benzoyl peroxide.

This material, suited for the fabrication of dentures, may be cured at elevated temperature while being shaped. Suitable curing conditions are 130° C./10 min.

EXAMPLE 6

Pasty dental material in accordance with the invention

A pasty mixture is prepared by the procedure set forth in Example 3 from
260 g bead polymer according to Example 1,
80 g triethylene glycol dimethacrylate,
120 g bis-GMA, and
4 g benzoin isopropyl ether.

This material is extremely well suited for use as a dental filling material. It will cure when exposed to UV light (Uviolite lamp of the Espe company) within 40 sec in layers 3 mm thick.

What is claimed is:

1. A dental material in paste form consisting essentially of
   (1) at least one phase of at least one finely divided, cross-linked plastic wherein at least 50% by weight of said finely divided, cross-linked plastic is made from at least one ester of methacrylic acid and a monohydric or polyhydric alcohol, said crosslinked plastic comprising 40 to 80% by weight of the dental material and said cross-linked plastic being made from a monomeric mixture containing 2 to 35% by weight of crosslinking agent and
   (2) a second phase consisting of polymerizable binder in which at least 50% by weight of said binder is at least one ester of methacrylic acid and a monohydric or polyhydric alcohol.
2. A dental material according to claim 1, in which the finely divided, crosslinked plastic is in the form of crosslinked polymer beads with an average particle size of 10 to 100μ.
3. A dental material in paste form according to claim 1 or 2 wherein the finely divided, crosslinked plastic is present in an amount from 50 to 75%.
4. A dental material according to claim 1, in which the finely divided, crosslinked plastic is produced from from at least one aliphatic or cycloaliphatic ester of methacrylic acid to the extend of more than 80% by weight.
5. A dental material according to claim 1 in which more than 80% by weight of said binder is at least one ester of methacrylic acid and a monohydric or polyhydric alcohol.

* * * * *